United States Patent
Swallert

(10) Patent No.: US 6,258,025 B1
(45) Date of Patent: Jul. 10, 2001

(54) ROTABLE LENS CLEANING DEVICE

(75) Inventor: Sven A. Swallert, Geneva (CH)

(73) Assignee: Medifront AB (SE)

( * ) Notice: Subject to any disclaimer, the term of this patent is extended or adjusted under 35 U.S.C. 154(b) by 0 days.

(21) Appl. No.: 09/341,732

(22) PCT Filed: Jan. 30, 1998

(86) PCT No.: PCT/SE98/00148

§ 371 Date: Jul. 15, 1999

§ 102(e) Date: Jul. 15, 1999

(87) PCT Pub. No.: WO98/35608

PCT Pub. Date: Aug. 20, 1998

(30) Foreign Application Priority Data

Jan. 31, 1997 (SE) .................................................. 9700292

(51) Int. Cl.⁷ ........................................................ A61B 1/12
(52) U.S. Cl. .......................... 600/157; 600/129; 600/156; 600/176; 600/175
(58) Field of Search .................................. 600/175, 176, 600/129, 156, 157

(56) References Cited

U.S. PATENT DOCUMENTS 5,647,840 * 7/1997 D'Amelio et al. .................... 600/169
5,894,369 * 4/1999 Akiba et al. ........................... 359/820

FOREIGN PATENT DOCUMENTS 2803897  8/1979 (DE) .
7064012  3/1995 (JP) .

* cited by examiner

Primary Examiner—Linda C. M. Dvorak
Assistant Examiner—Jocelyn Ram
(74) Attorney, Agent, or Firm—Ostrolenk, Faber, Gerb & Soffen, LLP

(57) ABSTRACT

The invention relates to a device having an orifice covered by an optical device (3), which is to be prevented from being dirtied. For that reason the device comprises a housing (1), in which a ring-shaped socket (2) supporting the optical device is rotatably journalled by means of a bearing arranged around the periphery of a socket (2). Moreover, the socket (2) is provided with a rim turbine blades (8) against which one or more jets of pressure air from nozzles (10, 11) in the housing (1) are directed.

9 Claims, 1 Drawing Sheet

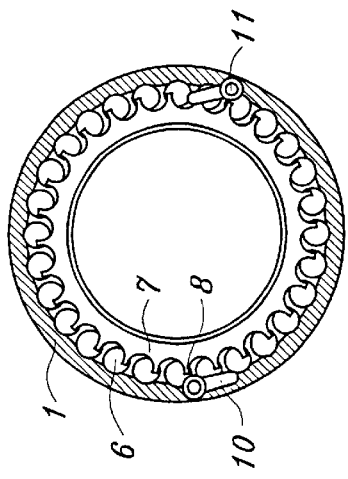
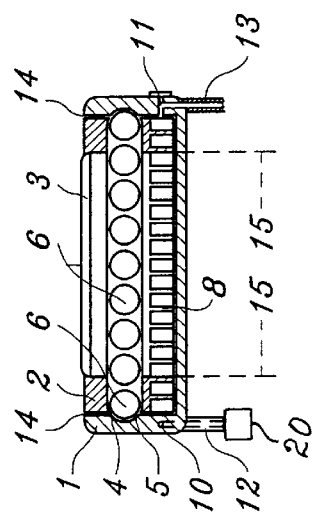
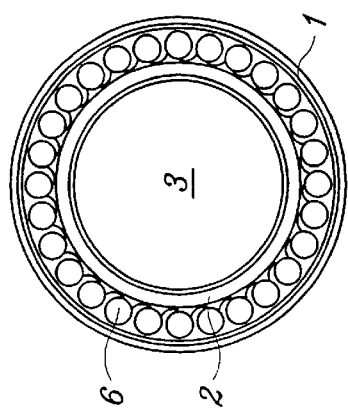
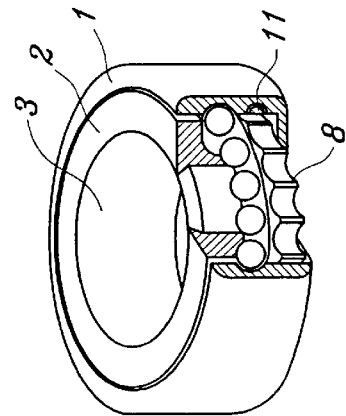

ROTABLE LENS CLEANING DEVICE

BACKGROUND OF THE INVENTION

The present invention relates to a device having an orifice covered by an optical device in the shape of a disk of glass or a lens, which is intended for being exposed to dirtying reducing the transparency, which dirtying may be for all splash of liquid.

Such devices are frequent in connection with operarating instruments for among others the more and more common so called laparotomy, and in fiber optical equipment. The use of such instruments and equipment is made difficult, however, when the optical device becomes dirtied by for example blood or other body fluids during surgical operations or medical examinations.

SUMMARY OF THE INVENTION

The object of the invention is to achieve a device of the kind mentioned by way of introduction in which the cleaning problem is solved in a simple and effective way.

This is obtained according to the invention in that the device comprises a housing in which a ring-shaped socket is rotatably mounted or journalled. The socket supports the optical device and comprises a rim of turbine blades to which at least one jet of pressure gas, preferably pressure air, is directed from a nozzle attached to the housing for effecting a rapid rotation of the ring-shaped socket and the optical device. Due to the rotation of the optical device, said device is kept clean in a manner known per se, but it is effected according to the invention by a journalling of the optical device such that the transparency of the most important part, i.e. the central portion, of the optical device is not disturbed. The way of mounting or journalling also makes it possible to rotatably journal an optical device of a diameter of only a few millimeters.

A bearing is suitably journalled between the ring-shaped socket and the housing, which bearing comprises a rim of rolling members, preferably balls, positioned partially in a circumferential groove around the ring-shaped socket, partially in a corresponding groove in the housing. The ring-shaped socket may be journalled in the housing, as an alternative, by a magnetic bearing, especially if the ring-shaped socket and the optical device have small sizes and a low weight. It is also possible to use a bearing of the air support type, preferably an air lubricated slide bearing.

The pressure gas leaving the rim of turbine blades is, according to a preferred embodiment of the invention, arranged to pass out from the front side of the optical device through a gap between the ring-shaped socket and the housing, such that the movable part is kept free from penetrating impurities between the movable part and the stationary housing. If necessary, it may be suitable to have the pressure gas passing through a heating device before it is supplied to said nozzle or nozzles, especially if the device is exposed to moisture and cold, for instance when used as a look through window-pane of a craft or vehicle. The heated air prevents the movable and stationary parts from freezing together.

BRIEF DESCRIPTION OF THE DRAWINGS

The invention is explaned in more detail in the following description with reference to the accompanying drawing schematically showing by way of example an embodiment of the device according to the invention, in which FIG. 1 is a plan view, FIG. 2 is a view from below with a bottom plate removed for the sake of clarity of the embodiment shown in perspective in FIG. 3.

FIG. 3 shows a perspective view with a sector removed for showing the interior of the device, and FIG. 4 is a cross-section of the housing of the device and the upper part of the socket of the optical device with only a small number of the balls of the bearing and the turbine blades shown.

DESCRIPTION OF A PREFERRED EMBODIMENT

The device shown in the drawing has a housing 1 and in the housing a rotatably mounted or journalled, ring-shaped socket 2, which both are made of transparent plastic material. An optical device in the shape of a glass disk 3 is attached to the socket 2. The socket 2 is also provided with a circumferential groove 4 and the housing 1 with a corresponding groove 5, in which grooves 4,5 steel bearing balls 6 are positioned. A rim 7 of metallic turbine blades 8 is attached to the bottom side of the socket 2. As indicated schematically in FIG. 2 two nozzles 10,11 directed tangentially towards the turbine blades at two diametrically opposed places of the housing are provided with axially directed connections 12,13 for pressure air, which connections are shown in FIG. 4. One 11 of the nozzles 10,11 is also shown in cross-section in FIG. 3.

At supply of pressure air to the nozzles 10,11 two jets of pressure air are directed towards the turbine blades 8 such that the rim 7 and the socket 2 together with the glass disk 3 are rotated, guided by the bearing balls 6. The pressure air flows via the turbine blades 8 and leaves through a gap 14 between the socket 2 and the housing 1.

The device may be intended for a place at the point of a tubular surgical instrument and behind the bottom plate of the housing 1, or if the bottom plate is provided with an aperture, behind the glass disk a be equipped with a micro camera or a fiber optical device. Blood and other body fluids or substances that get into contact with the rapidly rotating glass disk 3 are thrown off, and the glass disk is kept clean from all that can decrease the visibility.

Due to the fact that the rotative optical device 3 is journalled along the outer periphery of the ring-shaped socket 2, the visibility of the device essentially coincides with the entire area of the optical device 3, which area is marked by the dashed lines 15 which also indicate where the aperture of the bottom plate of the housing 1 should be placed if the housing should be made of metal.

The invention is of course not limited to the example of an embodiment shown and described but can be modified in various ways within the scope of the device defined by the patent claims. Hence, the shown bearing device may, as an alternative, be designed like a magnetic bearing or an air supporting bearing, which bearings are well known to the skilled person. As the device according to the invention also can be used as a look-through window pane of vehicles or crafts it may be exposed to frost. Therefore the device suitably is equipped with a device 20 for heating the pressure air before it is supplied to the turbine blades and is directed out through the gap 14 between the rotating socket 2 and the housing 1.

What is claimed is:

1. A rotatable lens cleaning device comprising:
    an optical viewing disk or lens, which is intended to be exposed to dirtying substances that may reduce the visibility therethrough;

a housing having a ring shaped socket rotatably journalled in the housing, the socket supporting the optical viewing disk or lens;

the socket including a rim of turbine blades;

a nozzle attached to the housing for directing at least one jet of pressure gas at the blades for effecting rapid rotation of the socket and the optical viewing disk or lens thereon with respect to the housing.

2. The optical device of claim 1, wherein the optical viewing disk is glass.

3. The optical device of claim 1, wherein the pressure gas is pressure air.

4. The optical device of claim 1, further comprising a bearing journalled between the ring shaped socket and the housing for enabling rotation of the socket in the housing.

5. The optical device of claim 4, wherein the bearing comprises a rim of rolling members; a circumferential groove around the ring shaped socket and a corresponding opposing circumferential groove in the housing; and the rolling members being positioned partially in each of the grooves for being guided therethrough.

6. The optical device of claim 5, wherein the rolling members comprise a rim of balls.

7. The optical device of claim 1, further comprising an air lubricated sliding bearing mounting the ring shaped socket in the housing for rotation in the housing.

8. The optical device of claim 1, further comprising a gap between the ring shaped socket and the housing for enabling pressure gas leaving the rim of turbine blades to pass out from the optical device through the gap.

9. The optical device of claim 1, further comprising a heating device for the pressure gas arranged to heat the gas before said gas is supplied to the nozzle.

* * * * *